United States Patent [19]

Entwistle et al.

[11] Patent Number: 4,748,185
[45] Date of Patent: May 31, 1988

[54] 4-HYDROXYCOUMARIN DERIVATIVES

[75] Inventors: Ian D. Entwistle, Sittingbourne; Peter Boehm, Maidstone, both of England

[73] Assignee: E. I. Du Pont de Nemours and Company, Wilmington, Del.

[21] Appl. No.: 944,942

[22] Filed: Dec. 16, 1986

[30] Foreign Application Priority Data

Dec. 20, 1985 [GB] United Kingdom ............... 8531388

[51] Int. Cl.$^4$ .................... C07D 311/12; A61K 31/35
[52] U.S. Cl. ...................................... 514/457; 549/285
[58] Field of Search ....................... 549/285; 514/457

[56] References Cited
U.S. PATENT DOCUMENTS 2,427,578  9/1947  Stahmann et al. ................. 549/285
3,957,824  5/1976  Hadler et al. ..................... 549/285
4,520,007  5/1985  Entwistle et al. ................. 514/457

Primary Examiner—Jane T. Fan

[57] ABSTRACT

The invention provides 4-hydroxycoumarin compounds of general formula

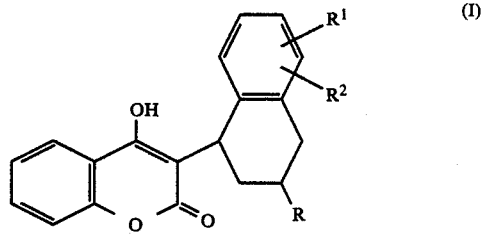

wherein $R^1$ and $R^2$ are independently selected from hydrogen and halogen atoms and R represents a group of formula

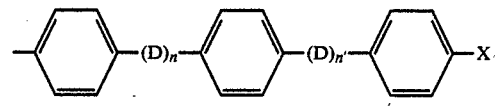

wherein one of n and n' is 0, the other being 0 or 1, D represents a moiety —O—, —(CH$_2$)$_m$— or —O(CH$_2$)$_m$— where m is 1 or 2 and X represents a substituent selected from hydrogen, halogen, CN, CF$_3$, OCF$_3$, C$_{1-6}$ alkyl and C$_{1-6}$ alkoxy moieties, provided that when n is 1 and D is —OCH$_2$—, X may additionally represent a phenyl group, optionally substituted in the 4-position by a substituent selected from halogen, CN, CF$_3$, OCF$_3$, C$_{1-6}$ alkyl and C$_{1-6}$ alkoxy moieties; their preparation and their use as rodenticides.

8 Claims, No Drawings

4-HYDROXYCOUMARIN DERIVATIVES

This invention relates to 4-hydroxycoumarin compounds, to processes for their preparation, to rodenticidal compositions containing them and to their use as rodenticides.

Warfarin, 3-(α-acetonylbenzyl)-4-hydroxycoumarin, is the earliest anti-coagulant rodenticide, and was disclosed in 1947 in U.S. Pat. No. 2,427,578.

Emergence of "warfarin resistant" strains of rodents has led to a need for new rodenticidal compounds to be discovered.

U.S. Pat. No. 3,957,824 (and the corresponding UK Pat. specification No. 1,458,679) discloses a class of rodenticidal 4-hydroxycoumarin derivatives which are 3-(3-substituted-1,2,3,4-tetrahydro-1-naphthyl)-4-hydroxycoumarin compounds of general formula

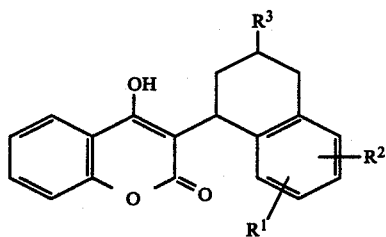

where $R^1$ and $R^2$ are the same or different and are hydrogen or halogen atoms, preferably chlorine or bromine, or alkyl or alkoxy groups, preferably having up to 6 carbon atoms, $R^3$ is an aryl group having the formula

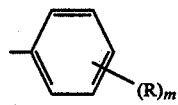

where m is 1 or 2, and R is the same or different and is a halogen atom, a straight or branched chain alkyl or alkoxy group, preferably containing at least 2, more preferably from 5 to 12 carbon atoms, a cycloalkyl, preferably cyclohexyl group, an aralkyl, preferably α-aralkyl group, a phenyl or a phenoxy group, or a halogeno, preferably para halogeno, substituted derivative thereof. The halogen atom or atoms are preferably chlorine or bromine. Where m is 1, R is preferably in the para position and when m is 2 one of the R groups is preferably in the para position. Preferably $R^3$ contains at least 1 but not more than 3 and optimally not more than 2 halogen atoms.

Two specific compounds of the above general formula are that wherein $R^1$ and $R^2$ are both hydrogen and $R^3$ is a 4-phenylphenyl group (difenacoum) and that wherein $R^1$ and $R^2$ are both hydrogen and $R^3$ is a 4-(4-bromophenyl)phenyl group (brodifacoum).

GB-A-2 126 578, and the corresponding EP-A-98 629, discloses a further class of 4-hydroxycoumarin derivatives having anticoagulant properties, particularly as rodenticides. In their broadest definition, these compounds are 3-(3-substituted-1,2,3,4-tetrahydro-1-naphthyl)-4-hydroxycoumarin compounds of the formula

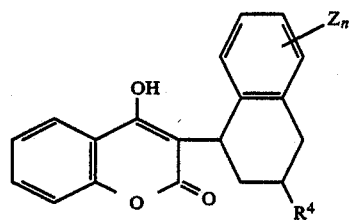

in which Z represents a halogen atom, preferably a chlorine atom, and n is 0, 1 or 2 and $R^4$ represents either (1) a grouping which comprises a phenylene radical attached directly or indirectly to the tetralin ring and having in the para position (with respect to such attachment) an electron-withdrawing atom or group whose rotational volume substantially does not exceed that of a phenyl group and which forms together with said phenylene radical a polarisable structure, or (2) a grouping selected from:

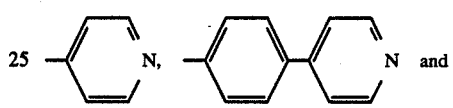

or (3) a grouping which comprises a phenylene radical attached directly to the tetralin ring and having in the para position (with respect to such attachment) a substituted furanyl or thiophenyl radical attached thereto directly or through oxygen and/or methylene, said furanyl or thiophenyl radical having an electron-withdrawing atom or group as a substituent in a position forming with the furanyl or thiophenyl radical a polarisable structure, said atom or group having a rotational volume which substantially does not exceed that of a phenyl group.

In the above formula V, $R^4$ is preferably more specifically defined as a group selected from

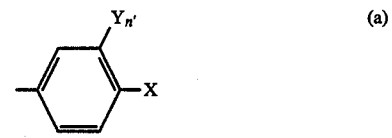

where X represents a halogen atom or a group CN, $NO_2$, $SO_2R^5$, $CF_3$, $OCF_3$, $COOR^5$ or $COR^5$, where $R^5$ is a $C_{1-6}$ alkyl group, n' is 0, 1 or 2 and Y is a fluorine or chlorine atom, provided that when X is halogen, n' is 1 or 2;

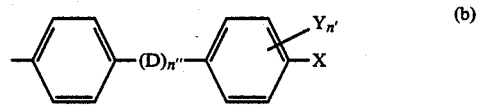

where X, n' and Y are as defined above, n" is 0 or 1 and D is an oxygen atom or a group $-O-(CH_2)_m-$, $-(CH_2)_m-O-$, $-O-(CH_2)_m-O-$, $-(CH_2)_m-O-(CH_2)_p-$, $-(CH_2)_{-m}$, or $-CH=CH-$, or a sulphur analogue thereof, wheren m is in the range 1 to 6 and p is in the range 1 to 6, provided that when n″ is 0 or 1, D is an oxygen atom and X is halogen, n′ is 1 or 2, and when n″ is 1 and D is —CH=CH—, X may additionally be a hydrogen atom;

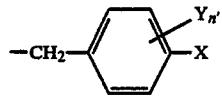

where X, N′ and Y are as defined above;
(d) a group selected from

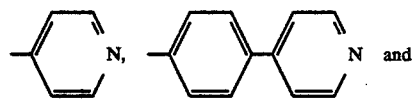

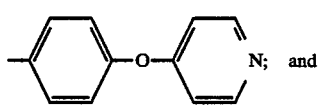

(e) a group selected from

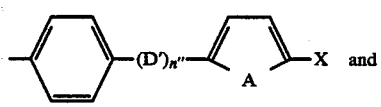

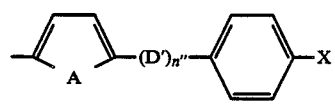

where X and n″ are as defined above, A is an oxygen or sulphur atom and D′ is an oxygen atom or a —CH₂— group.

The above described prior art 3-(3-substituted-1,2,3,4-tetrahydro-1-naphthyl)-4-hydroxycoumarin compounds all have a maximum of two phenyl or phenylene moieties. Surprisingly there has now been discovered a novel class of 4-hydroxycoumarin derivatives having useful (anticoagulant) rodenticidal properties.

According to the present invention there are provided 4-hydroxycoumarin compounds of general formula

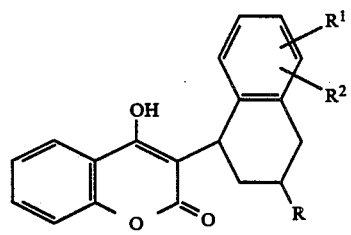

wherein R¹ and R² are independently selected from hydrogen and halogen atoms and R represents a group of formula

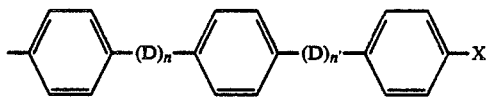

wherein one of n and n′ is 0, the other being 0 or 1, D represents a moiety —O—, —(CH₂)$_m$— or —O(CH₂)$_m$— where m is 1 or 2 and X represents a substituent selected from hydrogen, halogen, CN, CF₃, OCF₃, C$_{1-6}$ alkyl and C$_{1-6}$ alkoxy moieties, provided that when n is 1 and D is —OCH₂—, X may additionally represent a phenyl group, optionally substituted in the 4-position by a substituent selected from halogen, CN, CF₃, C$_{1-6}$ alkyl and C$_{1-6}$ alkoxy moieties.

A halogen atom represented by R¹ or R² is preferably a fluorine, chlorine or bromine atom. However it is preferred that R¹ and R² are both hydrogen atoms.

Preferably m is 1.

X preferably represents a hydrogen, fluorine, chlorine or bromine atom or a CN, CF₃, OCF₃, methyl or methoxy group or, when n is 1 and D is —OCH₂— X is a phenyl group; more preferably X represents a hydrogen, chlorine or bromine atoms or a CN or CF₃ group. Advantageously X represents a hydrogen, chlorine or bromine atom or a CF₃ group.

Those skilled in the art will appreciate that the compounds of formula I can exist in the form of individual isomers, mixtures of isomer pairs (e.g. "cis-" or "trans-" isomers) or mixtures of all possible isomers.

The invention also provides a process for preparing a 4-hydroxycoumarin compound of formula I as defined above which comprises thermally condensing 4-hydroxycoumarin with a compound of the general formula

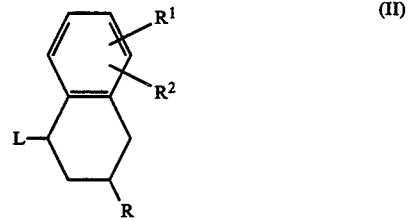

or the corresponding 1,2-dihydronaphthalene wherein R¹, R² and R are as defined above, and L is a hydroxy group or a halogen atom, preferably a bromine atom. Preferred compounds of formula II are those where L is a hydroxy group.

The compounds of formula II may be prepared by methods analogous to those described in the U.S. Pat. No. 3,957,824, UK Pat. specification No. 1,458,670, GB-A-2,126 578 and EP-A-98629 referred to above, for the preparation of 3-substituted-1,2,3,4-tetrahydro-1-naphthols. More specifically, the compounds of formula II may be prepared as described hereinafter in specific examples, or by methods analogous thereto, as will be readily understood by those skilled in the art.

4-Hydroxycoumarin may conveniently be thermally condensed with the compound of formula II at a temperatures in the range 60° C. to 170° C. Condensation may be effected with or without the use of a solvent. Thus the 4-hydroxycoumarin and compound of formula II may be reacted directly with one another, in the absence of solvent, typically at temperatures in the range 160° to 170° C. If a solvent is present, reaction may generally be effected at temperatures from 60° C. to reflux temperature, in the presence of a catalyst, e.g. sulphuric acid or a sulphonic acid.

Suitable solvents include, for example, acetic acid, formic acid and mixtures thereof, and liquid halogenated hydrocarbons having a boiling temperature of at least 60° C., e.g. chlorinated alkanes such as $C_{2-4}$ di- and trichloroalkanes. 1,2-dichloroethane (bp 83° C. to 84° C.) is very suitable, but other suitable chlorinated alkanes include 1,1,2-trichloroethane (bp 113° C. to 114° C.), 1,1,1-trichloroethane (bp 74° C. to 75° C.), 1,1-dichloropropane (bp 87° C.), 1,2-dichloropropane (bp 95° C. to 96° C.) and 1,3-dichloropropane (bp 125° C.).

Examples of sulphonic acids include methane sulphonic acid, trifluoromethane sulphonic acid and aryl sulphonic acids such as benzenesulphonic acid and p-toluenesulphonic acid.

Further in accordance with the invention there are provided a rodenticidal composition comprising a carrier in combination with, as active ingredient, a compound of formula I defined above; a method of exterminating rodents which comprises providing at a locus such a composition; and use of a compound of formula I as defined above as a rodenticide.

Compositions in accordance with the invention may contain up to 50% active ingredient, e.g. 0.0005 to 50% active ingredient. They may be in the form of a bait concentrate (which in use may be diluted by mixing with appropriate quantities of bait base), loose grain bait, block bait, pellet bait, suspension concentrate (which may be used in the preparation of gel formulations or progessively diluted by mixing with appropriate amounts of bait base), gel, tracking dust, or water bait.

The carrier may, according to the nature of the specific composition comprise one or more of a bait base (e.g. wheat, barley, oats, rye, maize, rice, millet, sorghum or pulses), an inorganic solid (e.g. chalk, china clay, gypsum, amorphous silica or diatomaceous earth) or water. A warning dye will usually be included for safety reasons. Flavourings (e.g. salt, mono-sodium glutamate, sugar, or saccharin) may also be included. Other additives which may be present in rodenticidal compositions include surfactants, oils, waxes, thickeners (e.g. polysaccharides), gums, and, if desired, chopped or minced vegetables or fruit.

The invention will be further understood from the following Examples.

EXAMPLE 1

Preparation of
3-{3-[4'-(4-trifluoromethylbenzyloxy)biphenyl-4-yl]-1,2,3,4-tetrahydro-1-naphthyl}-4-hydroxycoumarin (a) Phenylacetyl chloride (33.6 g) was added portionwise to a stirred solution of 4-methoxybiphenyl (40 g) in methylene chloride (300 ml) at 0° to 5° C. Powdered aluminium chloride (30.5 g) was added, and the resulting mixture was stirred at ambient temperature (20° C.) before being heated under reflux for 2 hours. The mixture was cooled and poured into ice in 2N aqueous hydrochloric acid. The mixture separated and the organic phase was washed with water and dried (MgSO$_4$). On partial evaporation a white solid crystallised out (18 g) which was purified by chromatography on silica using methylene chloride to give, as product, 4'-methoxybiphenyl-4-yl benzyl ketone (23%) mp 173° C.

(b) Sodium borohydride (1.25 g) was added portionwise to a stirred solution of the product of 1(a) above (5 g) in ethanol (75 ml) and methylene chloride (75 ml) at 40° C. The mixture was then stirred for 16 hours at ambient temperature (20° C.). Excess solvent was evaporated off and the mixture was added to water and extracted with methylene chloride. The methylene chloride extract was evaporated off to give, as product, 1-(4'-methoxybiphenyl-4-yl)-2-phenyl ethanol (5.0 g) mp. 110° C.

(c) Phosphorous tribromide (4 g) was added to a stirred solution of the product of 1(b) above (6 g) in methylene chloride (60 ml) at 0° to 5° C. This mixture was allowed to warm to 15° C. over 30 minutes and was then poured into a mixture of ice and water and extracted with methylene chloride. The methylene chloride extract was dried (MgSO$_4$) and evaporated below 30° C. to yield a solid residue (7.2 g) which was dissolved in toluene (100 ml) and N,N-dimethylformamide (5 ml) and added to a solution of sodio diethylmalonate (sodium hydride (1.4 g, 60% w/w) and diethylmalonate (6.4 g)) in toluene (40 ml) and N,N-dimethylformamide (10 ml) containing tetrabutylammonium bromide (100 mg). The resulting mixture was refluxed for 16 hours, poured onto water and extracted with toluene. The toluene extract was dried (MgSO$_4$) and evaporated to give a solid residue which was purified by chromatography on silica using methylene chloride as eluant to give, as product, 1,1-dicarbethoxy-2-(4'-methoxybiphenyl-4-yl)-3-phenylpropane (6.5 g) mp 63.9° C.

(d) The product of 1(c) above (35 g) was dissolved in a solution of sodium hydroxide (40 g) in water (500 ml) and ethanol (500 ml) and the resulting solution was refluxed for 4 hours. Excess ethanol was evaporated off and the resulting aqueous suspension was acidified with 2N aqueous hydrochloric acid. The solid which precipitated out was filtered off, washed with water and dried to give, as product, 1,1-dicarboxy-2-(4'-methoxybiphenyl-4-yl)-3-phenylpropane (26.5 g, 66%) mp 228° to 229° C.

(e) The product of 1(d) above (25 g) was refluxed in suspension in toluene (500 ml) containing quinoline (1 ml) for 1 hour. The resulting mixture was evaporated down to 150 ml, thionyl chloride (125 ml) was added, and the resulting solution was refluxed for 2 hours before evaporating off. The resulting solid residue was dissolved in toluene (250 ml), cooled to 0° C. with stirring, and a solution of stannic chloride (25 g) in toluene (25 ml) was rapidly added thereto in dropwise manner. The resulting dark brown mixture was stirred at 0° C. for 45 minutes and a mixture of concentrated aqueous hydrochloric acid and ice was added, followed by methylene chloride (50 ml). The mixture was stirred for 1 hours and solid material filtered off. The organic layer was separated, washed with water and with aqueous sodium hydroxide solution, dried (MgSO$_4$) and evaporated to give, as product, 3-(4'-methoxybiphenyl-4-yl)-3,4-dihydronaphthalen-1(2H)-one (16 g, 76%) mp 130° C.

(f) The product of 1(e) above (15.5 g) was refluxed in a mixture of glacial acetic acid (160 ml) and aqueous hydrobromic acid (48% w/w, 128 ml) for 7 hours. After cooling, the mixture was poured into ice and water and the precipitated solid was filtered off, washed with water and dried to give, as product, 3-(4'-hydroxybiphenyl-4-yl)-3,4-dihydronaphthalen-1(2H)-one (15 g) mp 193° C.

(g) The product of 1(f) above (0.01M), sodium hydroxide (0.02M), 4-trifluoromethylbenzyl bromide (0.011M) and "ADOGEN 464" (trade mark) (3 drops) ("ADOGEN 464", ex Aldrich Chemical Company, is a mixture of methyltri ($C_{8-10}$) ammonium chlorides, $n_D^{20}$1.4665) in methylene chloride (20 ml) containing water (1 drop) was refluxed for 5 hours. Water was then added and the organic phase was separated off, washed with water, dried (MgSO$_4$) and evaporated to give a solid residue which was purified by chromatography on silica using methylene chloride as eluant to give, as product, 3-[4'-(4-trifluoromethylbenzyloxy)biphenyl-4-yl]-3,4-dihydronaphthalen-1(2H)-one (3 g, 64%) mp 196.4° C.

(h) The product of 1(g) above (1 g) was heated at 40° C. in a mixture of methylene chloride (30 ml) and ethanol (15 ml) for 6 hours with sodium borohydride (0.5 g). The ethanol and methylene chloride were evaporated off, water was added and the mixture was extracted with methylene chloride. Evaporation of the extract gave, as product, 3-[4'-trifluoromethylbenzoyloxy)-biphenyl-4-yl]-1,2,3,4-tetrahydro-1-naphthol (1 g, 100%) mp 177° C.

(i) The product of 1(h) above (1 g), 4-hydroxycoumarin (0.7 g) and p-toluenesulphonic acid (0.25 g) in 1,2-dichloroethane (30 ml) were refluxed in a Dean-Stark apparatus for 24 hours. The resulting mixture was evaporated and the residue therefrom purified by chromatography on silica using methylene chloride as eluent to give, as product, a mixture of cis- and trans-isomers of 3-{3-[4'-(4-trifluoromethylbenzyloxy)biphenyl-4yl]-1,2,3,4-tetrahydro-1-naphthol}-4-hydroxycoumarin (1.25 g, 95%) mp 223° C.

Analysis: $C_{39}H_{29}O_4F_3$ requires: 75.4C, 4.8H; found: 75.7C, 4.7H.

EXAMPLE 2

Preparation of 3-{3-[4'-(4-cyanobenzyloxy)biphenyl-4-yl]-1,2,3,4-tetrahydro-1-naphthyl}-4-hydroxycoumarin (a) The reaction of 1(g) above was repeated using 4-cyanobenzylbromide in place of the 4-trifluoromethyl compound. 3-[4'-Cyanobenzyloxy)biphenyl-4-yl]-3,4-dihydronaphthalen-1(2H)-one (1.7 g, 39.5%) mp 170° C. was obtained as product.

(b) The reaction of 1(h) above was repeated using the product of 2(a) in place of that of 1(g). 3-[4'-(4-Cyanobenzyloxy)biphenyl-4-yl]-1,2,3,4-tetrahydro-1-naphthol (0.75 g, 75%) mp 172° C. was obtained as product.

(c) The reaction of 1(i) above was repeated using the product of 2(b) in place of that of 1(h). 3-{3-[4'-(4-Cyanobenzyloxy)biphenyl-4-yl]-1,2,3,4-tetrahydro-1-naphthyl}-4-hydroxycoumarin (0.55 g, 80%) mp 127° C. was obtained.

Analysis: $C_{39}H_{29}NO_4$ requires: 81.1C, 5.0H, 2.8N; found: 81.4C, 5.1H, 2.4N.

EXAMPLE 3

Preparation of 3-{3-[4'-(4-bromobenzyloxy)biphenyl-4-yl]-1,2,3,4-tetrahydro-1-naphthyl}-4-hydroxycoumarin (a) The reaction of 1(g) above was repeated using 4-bromobenzylbromide in place of the 4-trifluoromethyl compound. 3-[4'-(4-Bromobenzyloxy)-biphenyl-4-yl]-3,4-dihydronaphthalen-1(2H)-one (1.28 g, 27%) mp 191° C. was obtained as product.

(b) The reaction of 1(h) above was repeated using the product of 3(a) in place of that of 1(g). 3-[4'-(4-Bromobenzyloxy)biphenyl-4-yl]-1,2,3,4-tetrahydro-1-naphthol (0.78 g, 78%) mp 178° C. was obtained as product.

(c) The reaction of 1(i) above was repeated using the product of 3(b) in place of that of 1(h). 3-{3-[4'-(4-Bromobenzyloxy)biphenyl-4-yl]-1,2,3,4-tetrahydro-1-naphthyl}-4-hydroxycoumarin (0.6 g, 48%) mp 240° C. was obtained.

Analysis: $C_{38}H_{29}O_4Br$ requires: 72.2C, 4.6H; found: 72.2C, 4.8H.

EXAMPLE 4

Preparation of 3-[3-(4'-terphenyl-4-yl)-1,2,3,4-tetrahydro-1-naphthyl]-4-hydroxycoumarin (a) Aluminium chloride (28 g, powdered) was added portionwise to a stirred mixture of p-terphenyl (46 g) and phenylacetyl chloride (31 g) in methylene chloride (300 ml) under nitrogen at 0° to 5° C. The resulting mixture was stirred for two hours at 5° to 10° C. and for a further hour at ambient temperature (20° C.), after which it was poured into ice in 2N aqueous hydrochloric acid. Methylene chloride was added. A white solid precipitate was filtered off, the remaining mixture separated and the organic phase was washed with water, dried (MgSO$_4$) and evaporated to yield a crude mixture (61 g) of 4-phenacetyl-4'-terphenyl containing some bisphenacetylated by-product.

(b) Sodium borohydride (4 g) was added portionwise to a partial suspension of the product of 4(a) above (20 g) in 1,1,2-trichloroethane (11) and ethanol (120 ml) with stirring at 95° to 100° C. Stirring at 95° to 100° C. was continued for 4 hours, the mixture was evaporated and the resulting residue was washed with water and recrystallised from chloroform to give, as product, 1-(4'-terphenyl-4-yl)-2-phenyl ethanol (14.6 g, 62.7%) mp 197° C.

(c) Phosphorous tribromide (5 g) was added portionwise to a stirred solution of the product of 1(b) above (9.3 g) in methylene chloride (250 ml) and N,N-dimethylformamide (30 ml) at 0° C. The solution was allowed to warm to 15° C. over 1 hour and was then poured into ice water. Precipitated solid material was separated off, mixed with N,N-dimethylformamide and added to the separated organic phase. The resulting organic mixture was dried (MgSO$_4$) and evaporated below 35° C. to low volume (ca. 30 ml). Toluene (80 ml) was added to the resulting suspension and the resulting mixture was added to a solution of sodio diethylmalonate formed by dissolving sodium hydride (2 g) in toluene (60 ml) containing diethylmalonate (8.6 g), tetrabutylammonium bromide (200 mg) and N,N-dimethylformamide (10 ml). The resulting mixture was refluxed for 16 hours, and then poured into water. Solid material formed was filtered off and the separated organic phase was evaporated to give an oil. This oil was refluxed with sodium hydroxide (12 g) in ethanol (150 ml) and water (150 ml) for 6 hours. On cooling, excess ethanol was evaporated off, the mixture was diluted with water and extracted with diethyl ether to remove hydrocarbons. The aqueous phase was acidified with 2N aqueous hydrochloric acid. The solid which precipitated out was filtered off and recrystallised from acetonitrile to give, as product, 1,1-dicarboxy-2-(4'-terphenyl-4-yl)-3-phenylpropane (4.5 g, 38.8%).

(d) The product of 4(c) above (4 g) was refluxed in toluene (100 ml) with quinoline (0.5 g) for 4 hours. After cooling, thionyl chloride (40 ml) was added and the mixture was refluxed for 1 hour before evaporating off. The residue therefrom was dissolved in dry toluene (80 ml), cooled to 0° C. with stirring, under nitrogen, and a solution of stannic chloride (4 g) in toluene (4 ml) was rapidly added thereto in dropwise manner. The mixture was stirred rapidly for 1 hour at 0° C., and ice and concentrated hydrochloric acid were added. The mixture was stirred for 1 hour and the organic phase was then separated, washed with 2N aqueous sodium hydroxide and with water, dried (MgSO4) and evaporated to give a crude product which was purified by chromatography on silica using methylene chloride as eluant to give, as product, 3-(4'-terphenyl-4-yl)-3,4-dihydronaphthalen-1(2H)-one (0.5 g, 14%) mp 177° C.

(e) Sodium borohydride (250 mg) was added to a stirred mixture of the product of 4(d) above (0.5 g) in methylene chloride (30 ml) and ethanol (15 ml) at ambient temperature (20° C.). After 4 hours stirring, the mixture was evaporated, water was added and the mixture was extracted with methylene chloride. The extract was dried (MgSO4) and evaporated to give, as product, 3-(4'-terphenyl-4-yl)-1,2,3,4-tetrahydro-1-naphthol (0.5 g) mp 162° C.

(f) The reaction of 1(i) above was repeated using the product of 4(e) in place of that of 1(h). 3-[3-(4'-Terphenyl-4-yl)-1,2,3,4-tetrahydro-1-naphthyl]-4-hydroxycoumarin (0.58 g, 84%) mp 142° C. was obtained.

Analysis: $C_{37}H_{28}O_3$ requires: 85.4C, 5.4H; found: 84.9C, 5.4H.

EXAMPLE 5

Preparation of
3-{3-[4-(4-phenylbenzyloxy)phenyl]-1,2,3,4-tetrahydro-1-naphthyl}-4-hydroxycoumarin (a) 3-(4-hydroxyphenyl)-3,4-dihydronaphthalen-1(2H)-one (prepared as described on Pages 20 and 21 of EP-A-98629) was reacted with 4-bromomethylbiphenyl under conditions analogous to those of 1(g) above giving, as product, 3-[4-(4-phenylbenzyloxy)phenyl]-3,4-dihydronaphthalen-1(2H)-one (49%) mp 156° to 157° C.

(b) The product of 5(a) was reduced under similar conditions to those of 1(h) above giving, as product, 3-[4-(4-phenylbenzyloxy)phenyl]-1,2,3,4-tetrahydro-1-naphthol (ca. 100%) mp 121°-122° C.

(c) The product of 5(b) (2 g) was heated at 160° to 170° C. with 4-hydroxycoumarin (1 g) for 45 minutes. The mixture was allowed to cool, dissolved in methylene chloride and purified by chromatography on silica using 3% v/v methanol in methylene chloride to give, as product, 3-{3-[4-(4-phenylbenzyloxy)phenyl]-1,2,3,4-tetrahydro-1-naphthyl}-4-hydroxycoumarin (0.5 g, 18%) mp 228°-229° C.

Analysis: $C_{38}H_{30}O_4$ requires: 82.9C, 5.4H; found: 82.8C, 5.4H.

EXAMPLE 6

Preparation of
3-{3-[4-(4'-bromobiphenyl-4-ylmethoxy)phenyl]-1,2,3,4-tetrahydro-1-naphthyl}-4-hydroxycoumarin (a) 4-Bromomethyl-4'-bromobiphenyl was reacted under the conditions of 5(a) above to give, as product, 3-[4-(4'-bromobiphenyl-4-ylmethoxy)phenyl]-3,4-dihydronaphthalen-1(2H)-one (46%) mp 187° C.

(b) The product of 6(a) was reduced under similar conditions to those of 5(b) above to give, as product, 3-[4-(4'-bromobiphenyl-4-ylmethoxy)phenyl]-1,2,3,4-tetrahydro-1-naphthol (ca. 100%) mp 149° C.

(c) The reaction of 5(c) above was repeated, using the product of 6(b) in place of that of 5(b), to give, as product, 3-{3-[4-(4'-bromobiphenyl-4-ylmethoxy)phenyl]-1,2,3,4-tetrahydro-1-naphthyl}-4-hydroxycoumarin (10%) mp 112° C.

EXAMPLE 7

Preparation of
3-{3-[4-(4'-chlorobiphenyl-4-yloxy)phenyl]-1,2,3,4-tetrahydro-1-naphthyl}-4-hydroxycoumarin (a) Potassium t-butoxide (20 g) was added to a solution of 4-chloro-4'-hydroxybiphenyl (mp 142° C., prepared as in J.A.C.S, 2219, 1964) (33 g) in methanol (200 ml). The resulting mixture was evaporated to dryness under reduced pressure and the solid residue obtained was mixed with p-bromotoluene (83 g), copper powder (1 g) and dimethylsulphoxide (80 ml). The resulting mixture was refluxed (190° C.) for 16 hours, potassium hydroxide (9 g) was added and the mixture was refluxed for a further 6 hours. After cooling, the mixture was poured into water and extracted with methylene chloride. The methylene chloride extract was washed with water, dried (MgSO4) and evaporated to give a crude product in the form of an oil which solidified on standing. This crude product was triturated with 60/80 petroleum ether to give 1-(4'-chlorobiphenyl-4-yloxy)-4-methylbenzene (10 g, 29%) mp 130° C.

(b) The product of 7(a) above (23 g), N-bromosuccinimide (17 g) and azobisisobutyronitrile (5 mg) were refluxed in carbon tetrachloride (300 ml) for 6 hours under exposure to light from a tungsten lamp. After cooling, solid material was filtered off, and the carbon tetrachloride solution was evaporated to give a brown solid residue which was mixed with hexamine (23 g) and refluxed for 4 hours in methylene chloride (200 ml). On cooling, solid precipitate formed. This precipitate was filtered off and refluxed with 50% v/v aqueous acetic acid (75 ml) for 6 hours. Concentrated hydrochloric acid (15 ml) was added and the mixture was refluxed for a further hour. The mixture was cooled and extracted with methylene chloride. The methylene chloride extracts were washed with water, dried (MgSO4) and evaporated to give a solid residue which was purified by chromatography on silica using methylene chloride as eluant to give, as product, 4-(4'-chlorobiphenyl-4-yloxy)benzaldehyde (12.2 g, 50%) mp 123° C.

(c) A solution of sec-butyloxycarbonylmethylene triphenyl phosphorane (16.5 g) in methylene chloride (50 ml) was added at ambient temperature (20° C.) to a stirred solution of the product of 7(b) above (11.5 g) in methylene chloride (100 ml). After stirring for 1 hour, the solution was evaporated and the residue purified by chromatography on silica using methylene chloride as eluant to give, as product, sec-butyl 4-(4'-chlorobiphenyl-4-yloxy)cinnamate (15 g, 95%) mp 109° C.

(d) A solution of benzyl chloride (11 g) in dry diethylether (150 ml) was added to a vigorously stirred suspension of magnesium turnings (12.5 g) in diethyl ether (100 ml) containing an iodine crystal as initiator, under nitrogen. On cessation of spontaneous refluxing the ethereal solution was decanted under nitrogen into a flask containing cuprous chloride (200 mg). To this mixture at 0° C. under nitrogen was added over 30 minutes a solution of the product of 7(c) above (14 g) in diethylether (150 ml). Stirring was continued for a further 15 minutes at ambient temperature (20° C.), and the solution was poured into an excess of saturated aqueous ammonium chloride solution. The ether layer was separated, washed with 0.5N hydrochloric acid and with water, dried (MgSO$_4$) and evaporated to give a solid residue (19.4 g) containing sec-butyl 3-[4-(4'-chlorobiphenyl-4-yloxy)phenyl]-4-phenyl butanoate. This residue (18 g) was refluxed with potassium hydroxide (36 g, 88%) in water (36 ml) and ethanol (100 ml) for 16 hours. The ethanol was evaporated off and the residual aqueous mixture was diluted with water and extracted with methylene chloride. The aqueous solution remaining was acidified with hydrochloric acid, the mixture was extracted with methylene chloride and the extracts were washed with water, dried (MgSO$_4$), and evaporated to give a residue (15 g) containing 3-[4-(4'-chlorobiphenyl-4-yloxy)phenyl]-4-phenylbutanoic acid. This residue (14 g) was refluxed in benzene (70 ml) with thionyl chloride (70 ml) for 1 hour. The mixture was evaporated and the residue was dissolved in benzene (28 ml), cooled to 0° C. and a solution of stannic chloride (14 ml) in benzene (14 ml) was added thereto with rapid stirring over 3 minutes. The resulting dark brown solution was stirred for 45 minutes at 0° C., ice and a mixture of chloroform (28 ml) and diethylether (3 ml) was added and the resulting mixture was stirred for 15 minutes at ambient temperature (20° C.). The mixture was then extracted with diethyl ether. The ether extracts were washed with water, dried (MgSO$_4$) and evaporated to give a crude product (17 g) which was purified by chromatography on silica using toluene as eluant to give, as product, 3-[4-(4'-chlorobiphenyl-4-yloxy)-phenyl]-3,4-dihydronaphthalen-1(2H)-one (7.1 g, 51%, on crude acid) mp 118° C.

(e) The reaction of 1(h) above was repeated using the product of 7(d) in place of that of 1(g). 3-[4-(4'-chlorobiphenyl-4-yloxy)phenyl]-1,2,3,4-tetrahydro-1-naphthol (95%) mp 156.4° C. was obtained as product.

(f) The reaction of 1(i) above was repeated using the product of 7(e) in place of that of 1(h). 3-{3-[4-(4'-chlorobiphenyl-4-yloxy)phenyl]-1,2,3,4-tetrahydro-1-naphthyl}-4-hydroxycoumarin (93%) mp 132° C. was obtained.

Analysis: C$_{37}$H$_{24}$ClO$_4$ requires: 77.8C, 4.7H; found: 77.0C, 4.7H.

EXAMPLE 8

Preparation of 3-{3-[4-(4'-bromobiphenyl-4-ylmethyl)phenyl]-1,2,3,4-tetrahydro-1-naphthyl}-4-hydroxycoumarin (a) To a stirred solution of 4-bromo-4'-benzylbiphenyl (96.9 g) (prepared as in Can. J. Chem. 52, 1974, 1230) and phenacetyl chloride (47 g) in methylene chloride (500 ml) was added ground aluminium chloride (44 g) at 0° C. under nitrogen. Stirring was continued for 3 hours at 0° to 10° C. and then for a further 20 hours at ambient temperature (20° C.). The resulting mixture was poured into ice in 2N aqueous hydrochloric acid and extracted with methylene chloride. The methylene chloride extracts were washed with water, aqueous sodium hydroxide solution, and again with water, were dried (MgSO$_4$), and were evaporated to give a residue which was recrystallized from n-propanol to give, as product, benzyl 4-(4'-bromobiphenyl-4-ylmethyl)phenyl ketone (89 g, 76%) mp 113° C.

(b) The reaction of 1(b) above was repeated using the product of 8(a) in place of that of 1(a), giving, as product, 1-[4-(4'-bromobiphenyl-4-ylmethyl)phenyl]-2-phenyl ethanol (80%) mp 119° C.

(c) Phosphorous tribromide (20 g) was added dropwise to a stirred solution of the product of 8(b) above (44.3 g) in methylene chloride (450 ml) at 0° C. under nitrogen. The mixture was allowed to warm to 18° C. over one hour and was then poured into a mixture of ice and water and extracted with methylene chloride. The methylene chloride extract was dried (MgSO$_4$) and evaporated to yield an oil which was dissolved in toluene (100 ml) and added to a solution consisting of sodium hydride (7 g, 60% w/w) toluene (100 ml), N,N-dimethylformamide (15 ml), diethyl malonate (32 g) and tetrabutylammonium bromide (200 mg). The resulting mixture was refluxed for 16 hours, allowed to cool, poured into water and extracted with chloroform. The chloroform extract was dried (MgSO$_4$) and evaporated to give a residue which was purified by chromatography on silica using toluene as eluant to give, as product, 1,1-dicarbethoxy-2-[4-(4'-bromobiphenyl-4-ylmethyl)-phenyl]-3-phenylpropane (40 g, 70%) mp 71° C.

(d) A mixture of the product of 8(c) above (30 g), sodium hydroxide (60) g, water (500 ml), ethanol (500 ml) and acetonitrile (100 ml) was refluxed for 8 hours. Evaporation of ethanol and acetonitrile gave an aqueous solution which was acidified by addition of 2N aqueous hydrochloric acid. After stirring for 30 minutes, the solid which precipitated out was filtered off, washed with water and dried to give, as product, 1,1-dicarboxy-2-[4-(4'-bromobiphenyl-4-ylmethyl)phenyl]-3-phenylpropane (25 g, 93%) mp 154.5° C.

(e) The product of 8(d) above (20 g) was refluxed in toluene (400 ml) containing quinoline (1 ml) for 4 hours. The resulting mixture was evaporated to give a residue. This residue (less 5 g) was mixed with thionyl chloride (75 ml) in toluene (75 ml) and refluxed for 2 hours before evaporating off. The resulting residue was dissolved in benzene (30 ml), cooled to 0° C. with stirring, and a solution of stannic chloride (15 ml) in benzene (15 ml) was added dropwise over 2 minutes. After stirring for a further 45 minutes, ice was added, followed by concentrated aqueous hydrochloric acid (25 ml) and diethyl ether (3 ml). After stirring for 15 minutes, water was added and the mixture was extracted with diethyl ether. Evaporation gave a black oily residue which was purified by chromatography on silica using toluene as eluant to give, as product, 3-[4-(4'-bromobiphenyl-4-ylmethyl)phenyl]-3,4-dihydronaphthalen-1(2H)-one (6.7 g, 38%) mp 119.2° C.

(f) The reaction of 1(h) above was repeated using the product of 8(e) in place of that of 1(g), giving, as product, 3-[4-(4'-bromobiphenyl-4-ylmethyl)phenyl]-1,2,3,4-tetrahydro-1-naphthol (95%) mp. 158° C.

(g) The reaction of 1(i) above was repeated using the product of 8(f) in place of that of 1(h). 3-3-[4-(4'-bromobiphenyl-4-ylmethyl)phenyl]-1,2,3,4-tetrahydro-1-naphthyl-4-hydroxycoumarin (92%) mp 230.5° C.

Analysis: C$_{38}$H$_{29}$O$_3$Br requires: 74.4C, 4.7H; found: 74.3C, 4.8H.

EXAMPLE 9

Preparation of 3-{3-[4-(4-biphenyl-4-ylbenzyloxy)phenyl]-1,2,3,4-tetrahydro-1-naphthyl}-4-hydroxycoumarin 3-{3-[4-(4-Biphenyl-4-ylbenzyloxy)phenyl]-1,2,3,4-tetrahydro-1-naphthyl}-4-hydroxycoumarin, mp 245°-248° C., was prepared by a process analogous to those of Examples 5 and 6.

EXAMPLE 10

Preparation of 3-{3-[4-(biphenyl-4-ylmethyl)phenyl]-1,2,3,4-tetrahydro-1-naphthyl}-4-hydroxycoumarin 3-{3-[4-(Biphenyl-4-ylmethyl)phenyl]-1,2,3,4-tetrahydro-1-naphthyl}-4-hydroxycoumarin, mp 118°-121° C., was prepared by a process analogous to that of Example 8.

EXAMPLE 11

Preparation of 3-{3-[4-(biphenyl-4-yloxy)phenyl]-1,2,3,4-tetrahydro-1-naphthyl}-4-hydroxycoumarin 3-{3-[4-(Biphenyl-4-yloxy)phenyl]-1,2,3,4-tetrahydro-1-naphthyl}-4-hydroxycoumarin, mp 124°-127° C., was prepared by a process analogous to that of Example 7.

EXAMPLE 12

Anticoagulant activity of the compounds of Examples 1 to 11 was determined by measurement of the prothrombin time, which is a measure of blood-clotting properties and is a reliable indicator of efficacy for an anticoagulant rodenticide. The procedure for measurement of prothrombin time is based on Quick et al, Am. J. Med. Sci., 190, 501 to 511, 1935.

Prothrombin times were determined according to the following specific procedures. Test compounds were dissolved in a mixture of polyethylene glycol 200 (i.e. polyethylene glycol of average molar mass 200) and triethanolamine (9:1 w/w) and serially diluted with the same solvent system to give concentrations of; 5.0, 2.5, 1.0, 0.9, 0.8, 0.7, 0.6, 0.5, 0.45, 0.40, 0.35, 0.30, 0.25, 0.2 and 0.1 milligrammes per milliliter (mgml$^{-1}$).

As these concentrations represent a known number of milligrammes per milliliter administration of any solution to the test animal at the rate of 1 milliliter per 1 kilogramme of bodyweight (eg. a 250 g rat is administered 0.25 ml) delivers a dose (in mg kg$^{-1}$) numerically equivalent to the concentration of that solution. In this instance the terms concentration and dose are synonymous.

Thus, appropriate doses were a range of at least three consecutive doses from the above series of concentrations which it was estimated would induce a range of prothrombin time elevations between 0 to 100% such that a dose-response curve could be constructed for that analogue.

The doses were injected into test animals (200 to 250 g Wistar-strain male rats) by the interperitoneal route. Three days after injection, blood was withdrawn by cardiac puncture whilst the animals were held under "Halothane" anaesthesia.

Three rats were used in each test of a particular compound and three prothrombin time determinations were carried out on each blood sample. Prothrombin times were determined using the modified one-step method of Quick. The percentage extension time of each prothrombin time was determined by assigning 0% extension time to an arbitrary prothrombin resting time of 12 seconds, and 100% extension time to a prothrombin time elevated to an arbitrary 212 seconds. Results were plotted on log-probability graph paper, the best-line fitted, and the prothrombin time ED50 read from the graph.

For some compounds, LD50 data has also been generated, as follows.

Compounds were dissolved in a mixture of polyethylene glycol 200 and triethanolamine (9:1 w/w) and serially diluted with the same solvent system to given concentrations of: 10.0, 4.64, 2.15, 1.00, 0.464, 0.215, 0.10, milligrammes per milliliter (mgml$^{-1}$).

As these concentrations represent a known number of milligrammes per milliliter, administration of any solution to the test animal at the rate of 1 milliliter per 1 kilogramme of bodyweight delivers a dose (in mgkg$^{-1}$) numerically equivalent to the concentration of that solution.

Thus appropriate doses were a range of four consecutive oral doses from the series of concentration sufficient to cause low group mortality at the lowest dose, and high group mortality at the highest dose. Acute oral LD$_{50}$'s were then determined by reference to the tables in Horns' paper "Simplified LD$_{50}$ (or ED$_{50}$) Calculations", Biometrics, 12, 311-322.

Results of these tests are given in the following table, which includes, as comparative data, values obtained for the commercial rodenticides warfarin and difenacoum.

TABLE

| Example | 3-day ED$_{50}$ (mg/kg) | LD$_{50}$ (mg/kg) |
| --- | --- | --- |
| 1 | 0.4 | 0.32–0.4 |
| 2 | 1.6 | |
| 3 | 0.74 | 0.4–1.0 |
| 4 | 0.55 | 1.0 |
| 5 | 0.4 | 0.4–1.0 |
| 6 | 0.72 | |
| 7 | 0.36 | |
| 8 | 0.37 | |
| 9 | 0.49 | |
| 10 | 0.52 | |
| 11 | 0.55 | |
| Warfarin | 5.2 | |
| Difenacoum | 0.56 | 1.80 |

The compounds of Examples 1 to 8 (active ingredient) may be incorporated in rodenticidal formulations as illustrated by the following composition examples.

(1) Bait Concentrates (Master mixes)

Bait concentrates are prepared having the following compositions:

| | | % w |
| --- | --- | --- |
| (a) | Active ingredient | 50 |
| | Salt (NaCl) | 10 |
| | Chalk | 25 |
| | "Gasil" (amorphous silica) | 5 |
| | Furocert Indigo Carmine (warning dye) | 10 |
| (b) | Active ingredient | 0.05 |
| | Salt | 10 |
| | Sugar | 10 |
| | "Aerosil-200" (amorphous silica) | 2 |
| | Furocet Indigo Carmine (warning dye) | 5 |
| | Milled barley (bait base) | 72.95 |

The active ingredient, warning dye and other ingredients were mixed together, and in the case of (b), homogeneously combined with bait base.

For use in simple solid baits, the resulting bait concentrates are diluted by mixing with appropriate quantities of bait base.

(2) Solid (Loose Grain) Baits

Solid, loose grain, baits are prepared having the following compositions:

|     |                                | % w     |
| --- | ------------------------------ | ------- |
| (c) | Active ingredient              | 0.025   |
|     | Sugar                          | 10      |
|     | "Silica HP21" (amorphous silica) | 1     |
|     | Helio Fast Blue (warning dye)  | 0.1     |
|     | Soya bean oil                  | 1       |
|     | Pin-head oatmeal (bait base)   | 87.875  |
| (d) | Active ingredient              | 0.0005  |
|     | Salt                           | 0.1     |
|     | Saccharin                      | 0.1     |
|     | "Silica HP21" (amorphous silica) | 0.1   |
|     | Helio Fast Blue (warning dye)  | 0.05    |
|     | Mineral Oil                    | 2.0     |
|     | Whole wheat (bait base)        | 97.6495 |

The active ingredient, warning dye and other ingredients are mixed together and then combined homogeneously with the bait base.

3. Solid (Block And Pellet) Baits

Solid, block and pellet, baits are prepared having the following compositions:

|     |                                | % w     |
| --- | ------------------------------ | ------- |
| (e) | Active ingredient              | 0.025   |
|     | Mono-sodium glutamate          | 0.5     |
|     | Solvent Blue-A (warning dye)   | 0.15    |
|     | "Syloid" (amorphous silica)    | 0.1     |
|     | Fish meal (bait base)          | 10      |
|     | Oat flour (bait base)          | 30      |
|     | Rye (bait base)                | 29.225  |
|     | Parafin wax                    | 30      |
| (f) | Active ingredient              | 0.0005  |
|     | Sugar                          | 7.5     |
|     | Lactose                        | 15      |
|     | Solvent Blue-A (warning dye)   | 0.15    |
|     | Maize flour (bait)             | 20      |
|     | Parafin wax                    | 57.3495 |

The active ingredient, warning dye and other ingredients are mixed together, combined homogenously with the bait base(s) and parafin wax and either compressed into 20 g water-resistant blocks in a mould, or extruded into pellets (4 mm dia.×7–15 mm length).

(4) Suspension Concentrates

Suspension concentrates are prepared having the following compositions:

|     |                                      | % w     |
| --- | ------------------------------------ | ------- |
| (g) | Active ingredient                    | 50      |
|     | Lignin sulphonate                    | 3       |
|     | Polyethylene polypropylene glycol    | 15      |
|     | Polysaccharide                       | 0.5     |
|     | Bentonite                            | 7.5     |
|     | Monoethylene glycol                  | 2.5     |
|     | Diphenyl Brilliant Blue (warning dye) | 0.1    |
|     | Water                                | to 100  |
| (h) | Active ingredient                    | 1       |
|     | Saccharin                            | 5       |
|     | Lignin sulphonate                    | 2.5     |
|     | Polymethyacrylate                    | 3       |
|     | Bentonite                            | 5       |
|     | Diphenyl Brilliant Blue (warning dye) | 0.1    |
|     | Water                                | to 100  |

The lignin sulphonate and bentonite are dispersed in the bulk of the water, the active ingredient is added to the resulting dispersion and the mixture is ground in a wet mill, before addition of the remaining ingredients and water to 100% and blending until homogeneous.

Suspension concentrates may be used in the preparation of gel formulations. Alternatively, for use in simple solid baits, the resulting suspension concentrates can be missed with quantities of bait base and the resulting solid concentrates homogeneously mixed with further appropriate quantities of bait base.

(5) Gels

Gels are prepared having the following compositions:

|     |                                  | % w    |
| --- | -------------------------------- | ------ |
| (i) | Active ingredient                | 5      |
|     | Sodium alginate                  | 10     |
|     | Calcium sulphate                 | 10     |
|     | Carboxypolymethylene             | 5      |
|     | Carboxypolymethylene             | 5      |
|     | Polysaccharide                   | 5      |
|     | Sodium stearate                  | 2      |
|     | Polypropylene glycol             | 5      |
|     | "Aerosil-200" (amorphous silica) | 20     |
|     | Chloramine Sky Blue (warning dye) | 0.5   |
|     | Water                            | to 100 |
| (j) | Active ingredient                | 0.005  |
|     | Polypropylene glycol             | 20     |
|     | "Aerosil-200" (amorphous silica) | 30     |
|     | Chloramine Sky Blue (warning dye) | 0.05  |
|     | Polyethylene glycol              | 40     |
|     | Carboxycellulose                 | 9.945  |

Surfactants components are mixed (where appropriate) with some of the water, the active ingredient is added, with grinding in a wet mill, and remaining ingredients are added and the gel blended until homogeneous.

Gels are injected into burrows and laid in rodent runs.

(6) Tracking Dusts

Tracking dusts are prepared having the following compositions:

|     |                                | % w   |
| --- | ------------------------------ | ----- |
| (k) | Active ingredient              | 5     |
|     | Direct Blue (warning dye)      | 2.5   |
|     | "Sipernat 17" (amorphous silica) | 1   |
|     | Gypsum (dust)                  | 91.5  |
| (l) | Active ingredient              | 0.05  |
|     | Direct Blue (warning dye)      | 0.1   |
|     | "Sipernat 17" (amorphous silica) | 0.5 |
|     | Basic slag (dust)              | 99.35 |

The active ingredient, warning dye and amorphous silica are homogeneously dispersed in the inorganic dust.

Tracking dusts are blown into rodent burrows or laid in patches 1 to 2 mm deep in rodent runs.

(7) Water Baits

Water baits are prepared having the following compositions:

|     |                              | % w    |
| --- | ---------------------------- | ------ |
| (m) | Active ingredient            | 0.025  |
|     | Sugar                        | 5      |
|     | Acacia gum                   | 10     |
|     | Sodium cellulose glycolate   | 5      |
|     | Paper Blue Dye (warning dye) | 0.025  |
|     | Water                        | to 100 |
| (n) | Active ingredient            | 0.0005 |
|     | Glycerol                     | 5      |
|     | Sorbitol                     | 5      |
|     | Triethanolamine              | 0.05   |
|     | Carboxymethylcellulose       | 2.5    |

| | % w |
|---|---|
| Polyoxyethylene sorbitan monolaurate | 2 |
| Water | to 100 |

The active ingredient is mixed with other ingredients to form a concentrate which is diluted with the water.

Water baits are most frequently used in dry environments such as warehouses and deep litter chicken houses, where rodents require a supply of drinking water.

What is claimed is:

1. A 4-hydroxycoumarin compound of formula

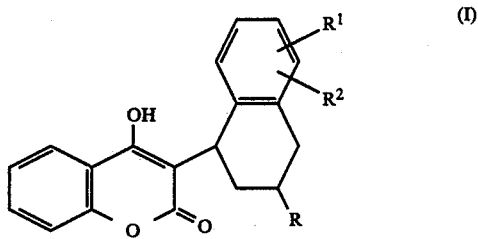

(I)

wherein $R^1$ and $R^2$ are independently selected from hydrogen and halogen atoms and R represents a group of formula

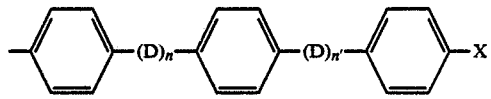

wherein one of n and n' is 0, the other being 0 or 1, D represents a moiety —O—, —(CH$_2$)$_m$— or —O(CH$_2$)$_m$— where m is 1 or 2 and X represents a substituent selected from hydrogen, halogen, CN, CF$_3$, OCF$_3$, C$_{1-6}$ alkyl and C$_{1-6}$ alkoxy moieties, provided that when n is 1 and D is —OCH$_2$—, X may additionally represent a phenyl group, optionally substituted in the 4-position by a substituent selected from halogen, CN, CF$_3$, OCF$_3$, C$_{1-6}$alkyl and C$_{1-6}$ alkoxy moieties.

2. A compound as claimed in claim 1 wherein $R^1$ and $R^2$ are both hydrogen atoms.

3. A compound as claimed in claim 1 or 2 wherein m is 1.

4. A compound as claimed in claim 1, 2 or 3 wherein X represents a hydrogen, fluorine, chlorine or bromine atom or a CN, CF$_3$, OCF$_3$, methyl or methoxy group, or, when n is 1 and D is —OCH$_2$—, X is a phenyl group.

5. A compound as claimed in claim 4 wherein X represents a hydrogen, chlorine or bromine atom or a CN or CF$_3$ group.

6. A compound as claimed in claim 5 wherein X represents a hydrogen, chlorine or bromine atom or a CF$_3$ group.

7. A rodenticidal composition comprising a carrier in combination with, as active ingredient, an effective amount of a compound of formula I according to claim 1.

8. A method of exterminating rodents which comprises providing at a locus a composition according to claim 7.

* * * * *